United States Patent [19]

Crais

[11] 4,398,907
[45] Aug. 16, 1983

[54] MULTIPLE OUTLET MICROARTERIAL BRIDGE FOR DIGITAL REPLANTATION

[76] Inventor: Thomas F. Crais, 3600 St. Charles Ave., New Orleans, La. 70115

[21] Appl. No.: 280,064

[22] Filed: Jul. 2, 1981

[51] Int. Cl.³ .............................................. A61M 5/00
[52] U.S. Cl. ........................................ 604/8; 604/173; 604/28; 128/334 R
[58] Field of Search ............ 128/214 R, 214 G, 214.2, 128/348–350, 334 R, 346; 604/4, 8, 28, 173

[56] References Cited

U.S. PATENT DOCUMENTS

| | | | |
|---|---|---|---|
| 2,674,265 | 4/1954 | Dennis | 128/214 R X |
| 2,697,435 | 12/1954 | Ray | 128/214.2 |
| 2,729,876 | 1/1956 | Hagemann | 27/24 A |
| 2,935,068 | 5/1960 | Donaldson | 128/348 |
| 3,435,824 | 4/1969 | Gamponia | 128/334 R |
| 3,490,438 | 1/1970 | Lavender et al. | 128/214 R X |
| 3,598,125 | 8/1971 | Cogley | 128/346 |
| 3,814,080 | 6/1974 | Norman | 128/346 X |
| 3,834,124 | 9/1974 | Ichikawa et al. | 128/214 R X |
| 4,257,416 | 3/1981 | Prager | 128/214 R |

FOREIGN PATENT DOCUMENTS 2309242 11/1976 France .............................. 128/214.2

Primary Examiner—Dalton L. Truluck
Attorney, Agent, or Firm—Thomas S. Keaty

[57] ABSTRACT

An apparatus and method for reestablishing and maintaining a blood supply to one or more severed digital arteries comprising: an elongated, flexible tubular means for insertion into a major artery which conveys blood to a reservoir means which controls the flow of blood from the tubular means to a blood distribution means which is further comprised of: a plurality of elongated tubes which are inserted into an artery of a severed digit to be reestablished and maintained with blood; and circumferential clamping means for forming a substantially fluid-tight connection of the tubes within each severed digital artery after insertion.

21 Claims, 5 Drawing Figures

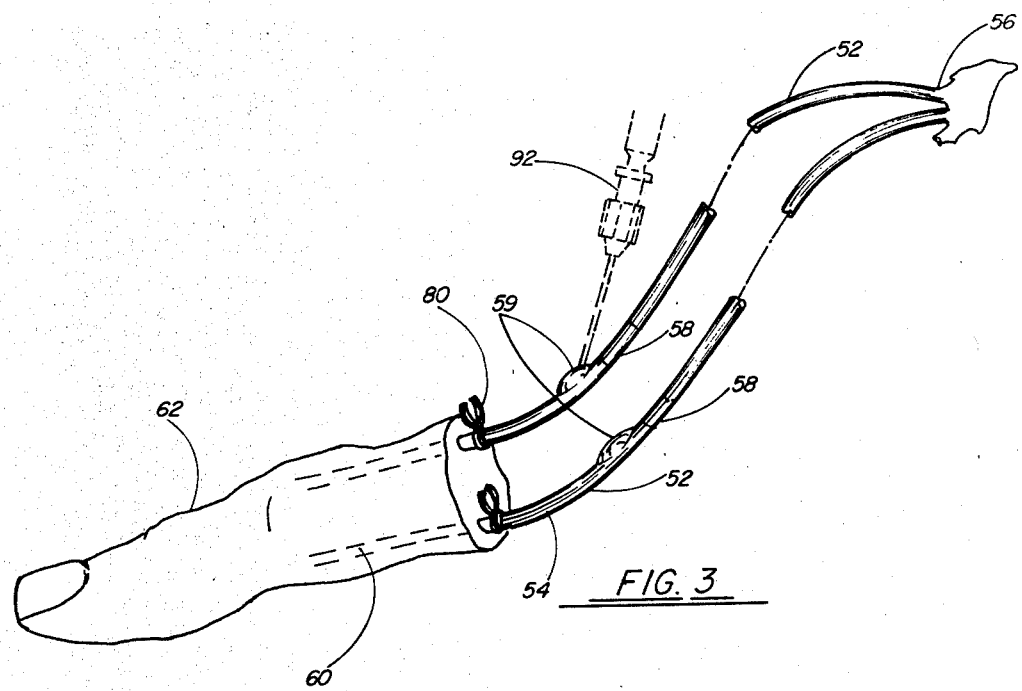
FIG. 3
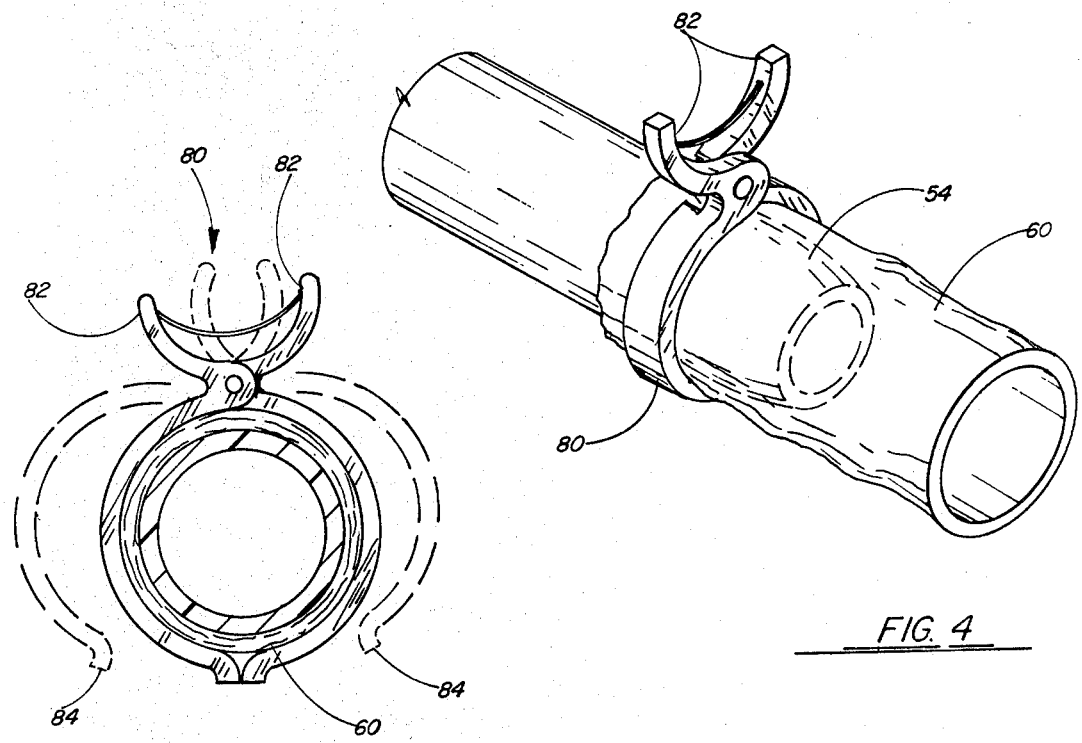
FIG. 4
FIG. 5

MULTIPLE OUTLET MICROARTERIAL BRIDGE FOR DIGITAL REPLANTATION

BACKGROUND OF THE INVENTION

1. Field of the Invention

The present invention relates to an apparatus and method for providing blood to severed body digits to re-establish and preserve them until they can be surgically replanted and reconstructed. The apparatus of the present invention more particularly relates to a multiple channel microarterial bridge or bypass for digital replantation comprising: a tube adapted for implantation in a major artery in the body which is connected to a blood reservoir in continuous free-flow to simultaneously provide or distribute blood to a plurality of tubes adapted to be implantable in the arteries of the severed body digits. In this regard, blood can be provided to several severed digits simultaneously as, for example, severed fingers.

2. General Background

The supply of blood to a severed body digit is of concern not only to the surgeon attempting to reattach and reconstruct the severed digit, but to the paramedical personnel transporting the injured party to a medical facility and those attending to the injured party in the emergency room. Time, distance, and the microscopic size of vessels are key factors in the reattachment and reconstruction of severed body digits. The lack of blood to the severed digits during such transportation, admittance to the hospital and replantation surgery can cause the death of the severed digits and therefore permanent loss of such by the injured party.

The time period between severance and completion of surgery also leaves the severed digit and the affected end of the body member subject to infection and therefore further complications.

Also, multiple trauma may exist which prevents the injured party from undergoing replantation and reconstruction surgery immediately since other surgery may be of a more urgent nature. Therefore, the crucial flow of blood to the severed digits may cover an extended period of time.

Cooling of the severed members may alleviate the problem to some degree, but the additional burdens of supply of suitable cooling material, the inability to compress the cooling material about severed digits to encompass its entire suface area, and the maintenance of the cooling material at a proper temperature all severely limit the use of this as a viable solution. Also, the use of ice which is the primary cooling material is wet and cold to the surgeon's hands when he must perform the delicate surgery needed on the microvascular system. In conclusion, ice as presently used has been an unsatisfactory solution to these problems.

The microscopic size of the vessels involved in digital reattachment and reconstruction surgery requires the surgeon to work with arteries which are less than one millimeter in diameter and which must withstand normal blood pressures in surgery. This surgery may last from 8-12 hours with each anastromosis taking 20-40 minutes, time again being of a critical nature.

If the flow of blood to the severed digits can be resumed within a reasonable time after severance and thereafter maintained until the completion of surgery, the chances of successful reattachment and reconstruction of the severed digit are greatly increased. The supply of blood, however, must be provided under suitable pressure and must be continuous in order to maintain the life of the severed digit.

There are several patents which show the use of tubes to convey blood from arteries to veinous members.

U.S. Pat. No. 3,826,257 discloses a shunt implantable in the human body to allow repeated access to blood in the circulatory system over a long period of time.

U.S. Pat. No. 3,882,862 discloses tubes to be sewn to severed arteries and veins to receive blood from the artery and return blood to the vein after hemodialysis.

U.S. Pat. No. 3,516,408 provides an arterial bypass for use in vascular surgery.

U.S. Pat. No. 3,853,126 provides for a shunt implantable in the body to provide external access to the arteries and veins.

U.S. Pat. No. 3,435,824 discloses a cardiovascular shunt used in heart surgery in which a portion of the blood circulatory system is to be bypassed. Tubes are insertable in vessels and sutured to secure such vessels during surgery.

U.S. Pat. No. 3,851,646 provides for tubes, which are inserted in major veins of the heart and tied or clamped thereto, allowing blood to flow to a pump oxygenator in a smooth coordinated flow.

U.S. Pat. No. 3,638,649 provides for an areteriovenous shunt permanently implantable, through the skin, to provide passage of blood for purposes of artificial dialysis and the like.

The present invention provides for a portable unit, attachable to the body and severed digits to provide simultaneously, under pressure, the continuous flow of blood to severed digits to retain their integrity while they are being reattached and reconstructed during surgery.

GENERAL DISCUSSION OF THE PRESENT INVENTION

The present invention provides a tapered sheathed needle for tapping a major artery of the body. This needle and its attendant tube are of such a size as will allow for a normal amount of blood flow into a blood reservoir which provides at least one, but up to five pairs of outlet channels or tubes (although only one pair of tube may be needed at any time) to distribute blood to the severed digits. The tubes will be conically tapered at their distal end to allow easy insertion into an artery of the severed digit or digits. The outlet tubes will be firmly retained in the severed digit artery by use of circumferential, non-compressing, non-crushing clamps which will fit onto the end of the outlet tubing.

The blood in the blood reservoir will be maintained at a pressure substantially equivalent to the normal pressure of blood in the severed digit by normal body blood pressure.

The apparatus in its preferred embodiment, should be a disposable unit which can be stored in a sterile bag until use. It can be transported to the scene of an accident, for instance, in an ambulance or by helicopter along with other emergency equipment and necessary instruments making it particularly valuable in a military application where time between injury, replantation and reconstruction may be long.

It is an object of the present invention to provide a device for use when a body has suffered the severing of one or more digits, so that a continuous and adequate flow of blood can be provided to the severed digit during either transportation or surgery to reattach and reconstruct the member.

It is another object of the present invention to provide a small, portable unit which can be instantly employed by trained medical personnel to temporarily perfuse a severed digit during delays in transporting the injured person to a surgical setting to shorten the time that the severed digit is without blood.

It is another object of the present invention, to provide a device for maintaining the life of a severed body digit without the attendant problems of using a cooling material such as ice which fails to adequately preserve the life of the severed member and does not maintain the supply of blood to the severed member and interferes with the surgeon's task.

Another object of the present invention is to provide an apparatus to supply several severed digits simultaneously with a fresh supply of blood so that reattachment and reconstruction of the digits can proceed sequentially without death of any one of the severed digits.

BRIEF DESCRIPTION OF THE DRAWINGS

For a further understanding of the nature and object of the present invention, reference should be had to the following detailed description, taken in conjunction with the accompanying drawings in which like parts are given like reference numerals and wherein:

FIG. 3 is a schematic perspective view of the device as it is adapted to a single severed finger.

FIG. 4 is an enlarged perspective view of the attachment of the device in an artery of a severed finger.

FIG. 5 is an end view of the circumferential clamping device of the apparatus of the present invention.

DETAILED DESCRIPTION OF THE PREFERRED EMBODIMENT

Figure 1:
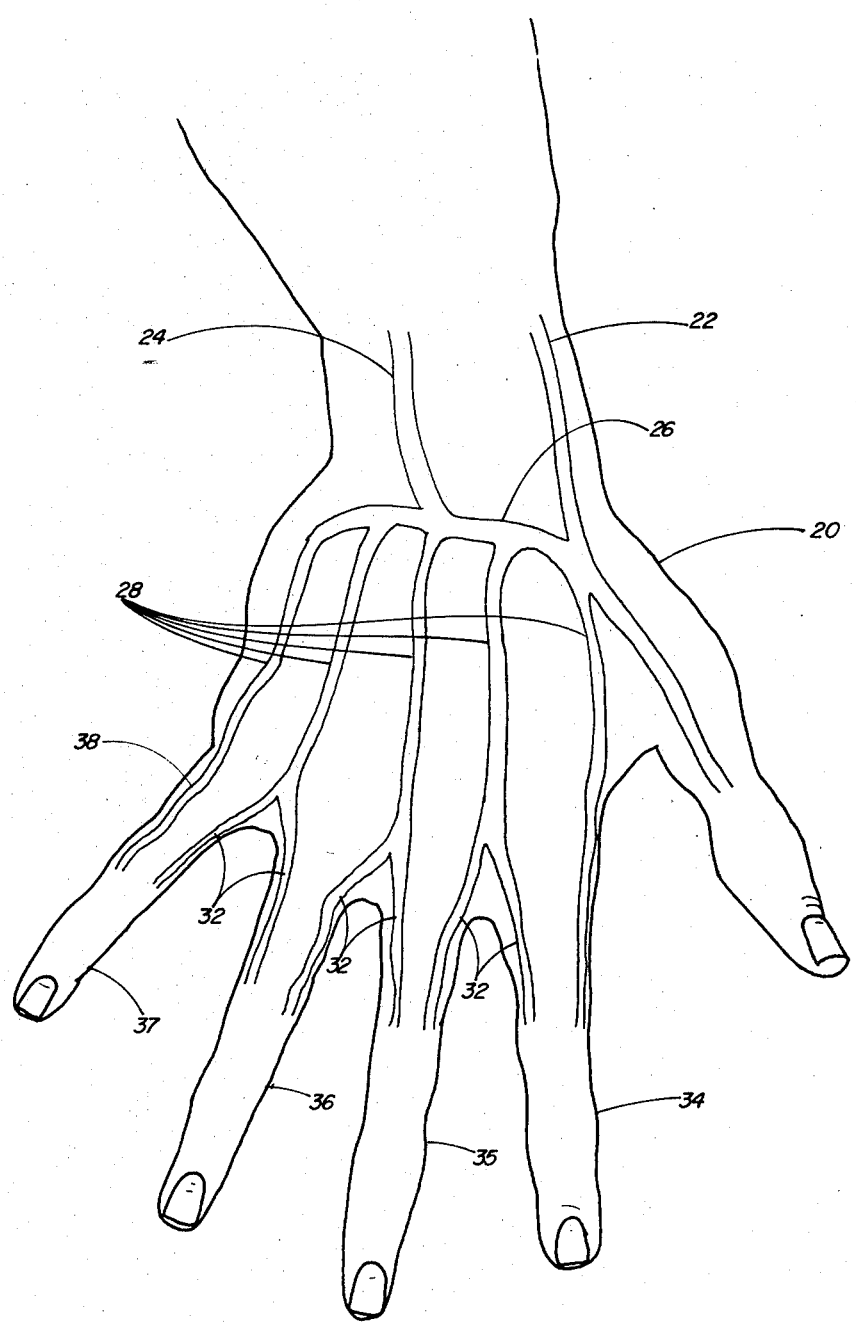
FIG. 1 is a schematic perspective view of a person's hand showing the principal arteries therein.

Although the multiple outlet microarterial bridge for digital replantation is illustrated in the drawings as providing a continuous flow of blood to the severed fingers on the hand, it should be understood that this device may be used for any of the severed digits of the body.

This invention relates to an arterial bridge or bypass useful in pre-plantation care of severed body digits and subsequently during surgery to reattach the severed digits and reconstruct the same. The device more particularly provides for substantially continuous, uninterrupted flow of blood from a major artery of the body through a first tube to a blood reservoir from which it is to be distributed to a series of microarterial tubes inserted in the arteries of the severed digits; the tubes being inserted in the lumen of the arteries and a substantially fluid-tight connection being formed by the use of non-crushing, non-compressing microclamps.

Figure 2:
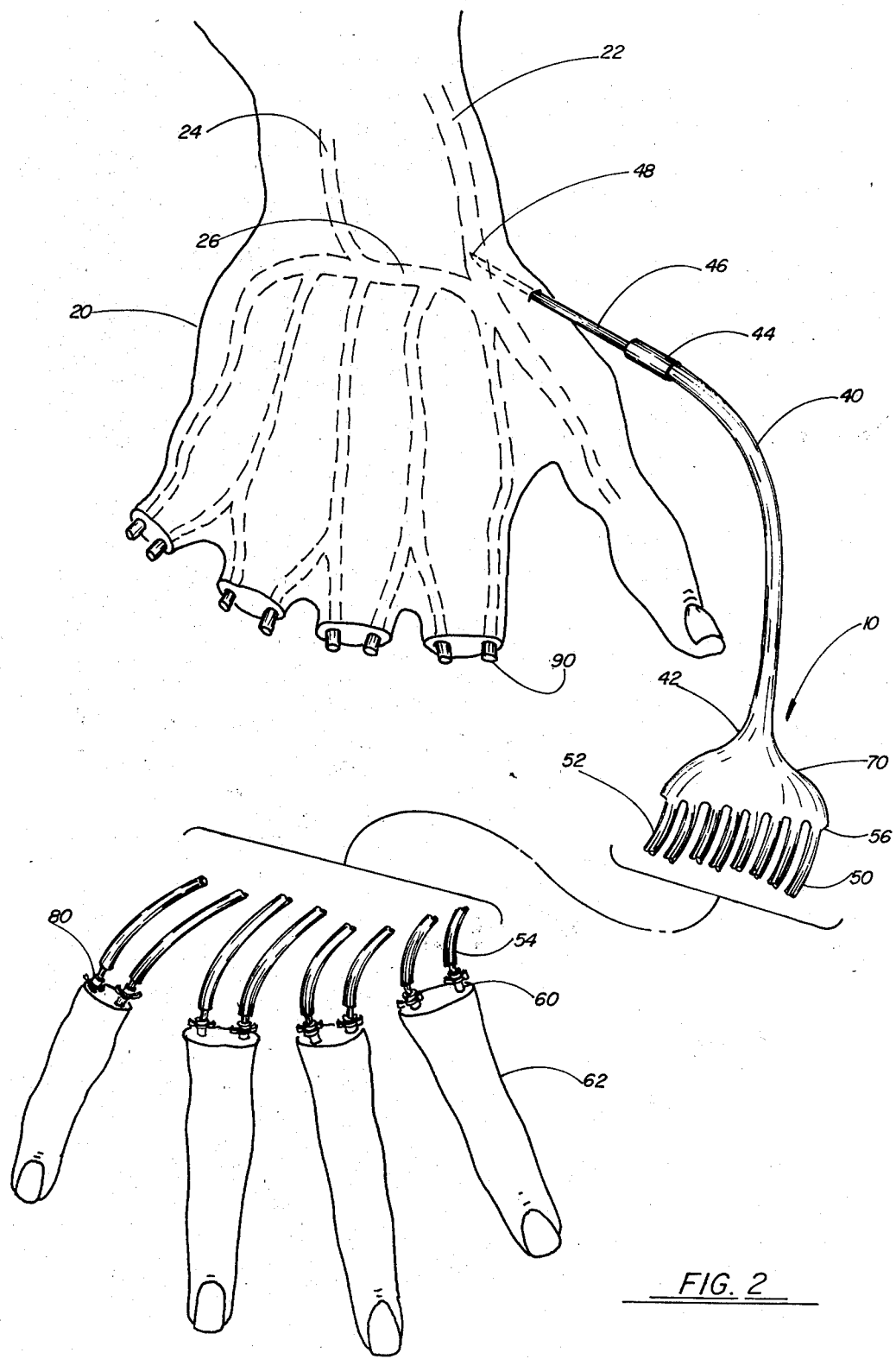
FIG. 2 is a schematic perspective view of a person's hand with four fingers severed therefrom showing the principal arteries therein and with the apparatus of the present invention implanted.

FIGS. 1 and 2 are simplified, schematic drawings of a hand and a hand with several (four in this case) fingers severed therefrom. FIG. 2 further shows the apparatus of the present invention implanted. Blood is supplied to the hand by two major arteries, the radial artery 22 and ulnar artery 24. The two arteries anastomose and complete the deep palmar arch 26. From the convexity of this arch arise the common palmar digital arteries 28 which proceed downward on the Lumbricales. Each receives the corresponding metacarpal artery and then divides into a pair of proper palmar digital arteries 32 which run along the continguous sides of the index 34, middle 35, ring 36 and little 37 fingers behind the corresponding distal nerves; they anastomose freely in the subcutaneous tissue of the finger tips and by smaller branches near the interphalangeal joints. The proper palmar digital artery for the medial side of the little finger 38 springs from the ulnar artery.

Upon severance of one or more of the body digits, preservation becomes critical. Especially if other trauma exists. Methods presently in existence employ the use of cooling materials, such as ice, to preserve the severed digits. The apparatus and method of the present invention is designed to attain preservation and the continued life of the severed digit via arterial perfusion. Arterial perfusion would be supplied by a major artery and transported via the invention to the severed digital artery thereby maintaining the life of the digit in anticipation of reattachment and reconstructive surgery. The apparatus and method of the present invention further uses the arterial bypass to maintain continuous and uninterrupted flow of blood under substantially constant pressure to the severed digit during this critical time. The device is further of a microscopic nature working with diameters of less than one millimeter.

Referring now to FIG. 2, which shows the replantation apparatus, indicated in general by the numeral 10, implanted, a first elongated flexible tubular member 40 with a proximal end 44 provides a needle means 46 adapted for insertion into a major artery such as radial artery 22. Tube 40 will convey blood to a reservoir 70, which is unitarily connected to the tube 40 at its distal end 42. The reservoir controls the flow of blood from this first tubular means to a blood distribution means 50 which is unitarily connected to reservoir 70. The blood distribution means 50 is further comprised of a plurality of separate flexible tubes 52 each of which have a distal end 54 adapted for insertion into an artery 60 of the severed body digit 62 which is to be reestablished and maintained with blood. The distal ends 54 of tubes 50 are secured in each artery 60 of the severed digit 62 by the use of non-crushing, non-compressing microvascular clamps, as for example clamp 80 which form a substantially fluid-tight attachment of such tubes in the severed arteries.

Referring further to FIG. 2, the first elongated flexible tube 40 is provided with a tapered, sheathed needle 46 at its proximal end 44. Needle 46 is convergently tapered at its end portion 48 for ease of insertion in a major artery such as radial artery 22. The patient's own blood will be provided at substantially standard blood pressure for conveyance of the patient's own blood to the severed body digit artery 60 across the area of severance. First elongated tube 40 is unitarily connected to reservoir 70 at its distal end 42. This unitary construction will provide a substantially continuous and uninterrupted flow of blood from artery 22 to reservoir 70. The diameter of reservoir 70 is greater than the diameter of tube 40 and will control the blood flow to distribution means 52. While the pressure across the reservoir 70 remains constant, the velocity of the blood will be stepped down or reduced. Reservoir 70 is unitarily connected to a plurality of channels or outlet tubes 52 at their proximal end 56. The combination of reservoir 70 and tubes 52 form a blood distribution means 50 being of a unitary construction. The smaller tubes 52 are of a microscopic nature being smaller in diameter than first elongated tube 40; the diameter of tubes 52 are on the order of 1 millimeter or less. Blood is further conveyed through blood distribution means 50 by tubes 52 to severed arteries 60 of severed digits 62. The distal ends 54 of tubes 52 are inserted in the lumen of the arteries 60 of severed digits 62. The distal end 54 is preferably convergently tapered to aid in insertion in the lumen, with the tubes being of such microscopic size. The pressure distribution across tubes 52 at their proximal end 56 will be substantially at a normal body blood pressure such as that existing at artery 22.

As further illustrated in FIG. 3, tubes 52 are inserted in severed articles 60 at their distal, convergently tapered end 54. To secure a substantially fluid-tight connection of tubes 52 within each of the severed body digit arteries 60 after insertion, clamp 80 is provided.

Clamp 80 is further illustrated in detail in FIGS. 4 and 5. It is a non-crushing, non-compressing microvascular ring type clamp with tabs 82 which, when forced inwardly together increase the diameter of such ring to allow disengagement of tube 52 from artery 60. A clamp of this nature dispenses with the requirement of suturing the severed artery to the tube and eliminates damage to the severed end which could create problems in further reconnection or reconstruction of the digit. The clamp 80 is therefore of a nature which will not crush or compress the artery during replantation procedures. Jaws 84 are used to stabilize the clamp and can be adjusted to insure flood-tight connection. The diameter of the clamp 80 itself must be of a diameter on the order of 1 millimeter.

Apparatus 10 is not implanted in the body except for tapered end 48 inserted in major artery 22 and the microarterial tubes 52 inserted in the lumen of the artery of a severed finger 62. The apparatus, except for clamps 80, are of a bio-compatible, flexible, silicone material and can be of a transparent material to further provide monitoring of the flow of blood. In an alternate embodiment not providing for the use of transparent material, a sight gage 58 as illustrated in FIG. 3 is provided as a means for observing the flow of blood in tubes 52. The sight gage 58 is provided by a portion of the length of each of the tubes 52 being made of transparent material. Further, each tube 52 is provided with vent area 59 adapted to either vent gas from the tube to prevent occlussion of the blood therein or pass medication (such as vasodilating or clot-dissolving drugs) into the tube, and therefore the flow of blood to dilate the vessels and prevent clotting of the blood. A conventional means, such as syringe 92, is used to inject such medication through vent area 59 and into the flow of blood in any of tubes 52.

When one or more severed digits exist the usefulness of the device can be further appreciated, as blood may be supplied to all the severed digits continuously and without interruption while the surgeon selects any one of the digits to be reconstructed and reattached to hand 20. When such digit is ready for reattachment, tube 52 is removed and clamped-off at its distal end portion.

Of course, while the apparatus of the present device is in use, the ends of severed veins 90 and the hand portion are clamped off by the use of any conventional clamping means. This will ensure maintaining normal blood pressure in major arteries, such as radial artery 22 which is providing blood to apparatus 10 for distribution to severed digit 62.

I claim:

1. An apparatus for reestablishing and maintaining a blood supply to one or more severed digital arteries, comprising:
   a. first elongated tubular means for conveying blood having proximal and distal end portions, said proximal end providing a needle means adapted for insertion of said proximal end into a major artery;
   b. blood distribution means comprising in part a plurality of elongated tubes, each of said tubes having a proximal and distal end portion, said distal end portion adapted for insertion into an artery of a severed digit to be reestablished and maintained with blood;
   c. reservoir means connecting the distal end of said tubular means with the proximal end of each of said tubes for controlling the flow of blood from said first tubular means to said blood distribution means;
   d. means associated with the distal end of each of said tubes for forming a substantially fluid-tight connection of the said tubes within each severed digital artery after insertion.

2. The apparatus of claim 1, wherein the needle means is convergently tapered to fit within the lumen of an artery.

3. The apparatus in claim 1, wherein the plurality of elongated tubes are of a diameter less than the said first elongated tubular means.

4. The apparatus of claim 1, wherein the plurality of elongated tubes are of a diameter of less than one millimeter.

5. The apparatus of claim 1, wherein the reservoir means is the unitary connection of the distal end portion of the first elongated tubular means and the blood distribution means.

6. The apparatus of claim 1, wherein the said reservoir means is of a diameter larger than the first elongated tubular means.

7. The apparatus of claim 1, wherein the blood distribution means provides blood to an artery of the severed digit under a pressure substantially equal to the pressure of blood in the said first tubular means.

8. The apparatus in claim 1, wherein the said distal end portion of each of the said elongated tubes are convergently tapered to fit within the lumen of a severed digital artery.

9. The apparatus of claim 1, wherein the means for forming a substantially fluid tight connection of said tubes within each severed digital artery is a circumferential non-crushing, non-compressing clamp.

10. The apparatus of claim 1, wherein at least a portion of the length of each of said elongated tubes is provided with a means for observing the flow of blood therein.

11. The apparatus of claim 1, wherein each of the said elongated tubes is provided with a means for venting gaseous matter from the said tube.

12. The apparatus of claim 1, wherein each of the said elongated tubes is provided with a means for passing medication into said tubes.

13. The apparatus of claim 1, wherein the said first elongated tubular means, blood distribution means and reservoir means are of a bio-compatible substance.

14. The apparatus in claim 13, wherein the bio-compatible substance is silicon.

15. The apparatus of claim 1, wherein the reservoir means provides a substantially continuous, uninterrupted flow of blood to the blood distribution means.

16. The apparatus in claim 1, wherein the said first elongated tubular means, said blood distribution means and said reservoir means are formed of a flexible, silicone material.

17. The apparatus of claim 1, wherein the first elongated tubular means, said blood distribution means, and said reservoir means are of a transparent material.

18. An apparatus for reestablishing and maintaining blood supply to one or more severed digital arteries, comprising:
   a. a first elongated flexible tubular means for conveying blood having proximal and distal end portions said proximal end providing a needle means convergently tapered for insertion of said proximal end into a major artery;
   b. blood distribution means comprising in part a plurality of elongated tubes, of a diameter less than said first elongated tubular means, each of said tubes having a proximal and distal end portion, said distal end portion convergently tapered for insertion into an artery of a severed digit to be reestablished and maintained with blood;
   c. reservoir means, of a diameter larger than the first elongated tubular means, connecting the distal end of said tubular means with the proximal end of each of said tubes for controlling the flow of blood from said first tubular means to said blood distribution means;
   d. circumferential clamping means associated with the distal end of each of said tubes for forming a substantially fluid-tight connection of the said tubes within each severed digital artery after insertion.

19. A method for reestablishing and maintaining the blood supply to one or more severed digital arteries comprising:
   a. inserting the proximal end of a first elongated tubular means for conveying blood into a major artery;
   b. connecting, by means of a reservoir, the distal end of said first tubular means with the proximal end of each of a plurality of elongated tubes of a blood distribution means;
   c. inserting the distal end of each of said elongated tubes within a severed digital artery; and
   d. forming a substantially fluid-tight connection of said elongated tubes within each severed digital artery after insertion.

20. The method of claim 19, wherein the proximal end of the said first elongated tubular means is provided with a needle means adapted for insertion of said proximal end into a major artery of the body.

21. The method of claim 19, wherein controlling the flow of blood from said first tubular means to said blood distribution means is by a reservoir means connecting the distal end of said tubular means with the proximal end of each of said tubes.

* * * * *